(12) United States Patent
Lévesque et al.

(10) Patent No.: US 6,397,680 B1
(45) Date of Patent: Jun. 4, 2002

(54) ULTRASONIC SPECTROSCOPY APPARATUS FOR DETERMINING THICKNESS AND OTHER PROPERTIES OF MULTILAYER STRUCTURES

(75) Inventors: Daniel Lévesque, Terrebonne; Marc Choquet, Saint-Bruno; Maroun Massabki, Mont-Royal, all of (CA)

(73) Assignee: National Research Council of Canada, Ottawa ( * ) Notice: Subject to any disclaimer, the term of this patent is extended or adjusted under 35 U.S.C. 154(b) by 10 days.

(21) Appl. No.: 09/624,077

(22) Filed: Jul. 24, 2000

(51) Int. Cl.[7] .......................... G01N 29/12; G01N 29/06
(52) U.S. Cl. ........................................ 73/602; 73/579
(58) Field of Search ...................... 73/579, 602, 582, 73/583, 627, 629, 630, 643

(56) References Cited
U.S. PATENT DOCUMENTS

| | | | | |
|---|---|---|---|---|
| 4,539,847 A | * | 9/1985 | Paap | 73/579 |
| 5,197,019 A | * | 3/1993 | Delon-Martin et al. | 73/602 |
| 5,303,590 A | * | 4/1994 | Modderman et al. | 73/588 |
| 5,408,881 A | * | 4/1995 | Piché et al. | 73/582 |
| 5,663,502 A | * | 9/1997 | Nagashima et al. | 73/599 |
| 5,812,261 A | * | 9/1998 | Nelson et al. | 356/318 |
| 6,092,419 A | * | 7/2000 | Dixon et al. | 73/602 |
| 6,128,081 A | * | 10/2000 | White et al. | 356/357 |

* cited by examiner

*Primary Examiner*—Hezron Williams
*Assistant Examiner*—Rose M. Miller
(74) *Attorney, Agent, or Firm*—Marks & Clerk

(57) ABSTRACT

An ultrasonic apparatus and method based on location of resonance frequencies is provided for determining unknown parameters in a multilayer structure, such as thickness, elastic properties of individual layers, or bonding strength between layers. Predicted resonance frequencies are obtained from the roots of a characteristic equation describing the multilayer structure. The predicted resonance frequencies are compared using a best-fit technique with the measured resonance frequencies to obtain the desired parameter. The method is of particular interest when ultrasound is generated by a laser and detected by either a contact ultrasonic transducer or a laser interferometer.

29 Claims, 6 Drawing Sheets

ULTRASONIC SPECTROSCOPY APPARATUS FOR DETERMINING THICKNESS AND OTHER PROPERTIES OF MULTILAYER STRUCTURES

BACKGROUND OF THE INVENTION

1. Field of the Invention

This invention relates to an ultrasonic apparatus and method based on resonance frequencies for determining unknown parameters in a multilayer structure, such as thickness, elastic properties of individual layers, or bonding strength between layers. The method is of particular interest when the thickness of the multilayer structure is less than two millimeters or when the ultrasound is generated by a laser.

2. Description of Prior Art

Ultrasonic measurement techniques generally refers to the principle of generating an ultrasonic pulse in an object, and then detecting the signal after propagation in the object to determine its geometrical, microstructural, and physical properties. This technique is advantageous because it is nondestructive. Conventional ultrasonic devices have been developed which involves the use of transducers, including piezoelectric and electromagnetic acoustic transducers (EMATs). Another ultrasonic device is based on laser-ultrasonics, wherein one laser with a short pulse is used for generation and another one, long pulse or continuous, coupled to an optical interferometer is used for detection. Either laser may be coupled through an optical fiber for ease of handling. This approach is advantageous because it does not require either the generation laser or the laser-interferometer detector to be close to the object. Furthermore, unlike an EMAT or piezoelectric transducer, the generation laser and laser-interferometer are not subject to precise orientation requirements. Details about laser-ultrasonics can be found in C. B. Scruby, L. E. Drain, "Laser-ultrasonics: techniques and applications", Adam Hilger, Bristol, UK 1990 and J. -P. Monchalin, "Optical detection of ultrasound," IEEE Trans. Ultrason. Ferroelectr. Freq. Control, 33,485 (1986).

To determine material properties from detected signal, usually the time of flight (TOF) method is used, which consists in measuring the time that the ultrasonic pulse takes to travel from the point of generation to the point of detection. This travel time relates to the travel distance and ultrasonic velocity which depends on some elastic properties, and knowing one parameter allows to get the other. For thickness measurement or properties in the thickness direction, the detection is made on the opposite side of the object aligned with the generation point, or on the same side and close to the generation point. This conventional method for determining properties of an object is limited to materials having a thickness which is relatively large compared to the wavelength of the ultrasonic pulse used. Otherwise, ultrasonic waves reflected from the front and back surfaces of a thin object (<2 mm) overlap and interfere in the time domain, precluding any measurement of time-of-flight. The generation of an ultrasonic pulse with smaller wavelength or high frequency content for cases of thin specimen may be limited by availability and costs associated with such an instrumentation.

The situation is even worst for multilayer structures comprising several layers of different materials with a finite bonding strength between layers. For multilayer structure with thick enough layers with respect to the ultrasonic wavelength, direct application of the TOF method is possible provided that a proper identification of reflected pulses is made with each layer. Recent examples are found in the U.S. Pat. No. 5,866,819 (Albu et al.) and U.S. Pat. No. 5,974,886 (Carroll et al.). For thinner multilayer structures, more refined techniques have been developed in recent years still analyzing the detected signal in the time domain. Examples of methods used are reduction of pulse duration with a deconvolution technique as found in the U.S. Pat. No. 5,723,791 (Koch et al.), comparison of detected waveform with a set of reference waveforms as in the U.S. Pat. No. 5,038,615 (Trulson et al.) and analyzing the interfering ultrasonic tone-bursts (narrowband signal, typically of about ten cycles in duration) with selected frequencies as in U.S. Pat. No. 5,608,165 (Mozurkewich).

The ultrasonic spectroscopy method is an alternative for this purpose. Closely related with the latter application, constructive or destructive interference between reflected tone-bursts at a particular frequency arising from propagation of an ultrasonic wave between the boundaries of the object corresponds to an ultrasonic resonance. For example, an ultrasonic resonance can arise in a plate when an ultrasonic wave propagates in the thickness direction and that the plate thickness corresponds to an integral multiple of half the wavelength of the ultrasonic wave. A longitudinal resonance refers to an ultrasonic resonance of a longitudinal wave, i.e., of an elastic wave polarized in the propagation direction. A shear resonance refers to an ultrasonic resonance of a shear wave, i.e., of an elastic wave polarized in a direction perpendicular to the propagation direction. In this method, a tone-burst is generated with a selected frequency, the signal detected is digitized and analyzed into the frequency domain typically by using the Fast Fourier Transform to get amplitude or phase information. By sweeping the frequency of the generated tone-burst and processing the each detected signal over the range of interest, the frequency response is obtained to identify resonances. Examples of applications using the frequency response but without relying on resonances are found in the U.S. Pat. No. 5,305,239 (Kinra), U.S. Pat. No. 5,663,502 (Nagashima et al.). Examples of those using the resonance information are found in U.S. Pat. Nos. 4,305,294 (Vasile et al.), 5,062,296 (Migliori), and more recently, U.S. Pat. No. 5,591,913 (Tucker). This method has the limitation of a long acquisition time as well as processing time, even with very recent improvements as in the U.S. Pat. No. 6,023,975 (Willis).

A different ultrasonic spectroscopy method is to launch a wideband pulse either with a transducer or with a radiation source like a laser and to analyze the single interaction signal comprising several reflected pulses or echoes into the frequency domain. The interference between overlapping echoes produces resonance dips or peaks in the amplitude of the frequency response. This method has been used with success, the overlapping of echoes can be very high, and the resonances are usually sharp enough to get a very good estimate of material properties, even with a moderately high level of attenuation. However, as in the previous method, this is mostly used for single plate or sheet of one material. A recent example from one of the inventors, measuring longitudinal as well as shear resonances with laser-ultrasonics to get material properties including texture in metal sheets, can be found in the U.S. Pat. No. 6,057,927 (Levesque et al.). For multilayer structure, an intricate coupling between resonance modes occurs which requires a more careful analysis to get any material properties. With the presence of a fluid between layers, the resonance modes are mainly those of individual layers in vacuum and an inversion algorithm has been successfully applied to recover some properties. For adhesively bonded layers, the resonance modes of the individual layers are strongly coupled and important frequency shifts are observed. The sensitivity of the ultrasonic signal to adhesive bond strength and the possibility of its determination is found in the U.S. Pat. No. 5,408,881 (Piche et Levesque), from one of the inventors. It is generally found that a model for propagation of ultrasound is essential to determine any unknown parameter from a multilayer structure.

It is an object of the present invention to alleviate the afore-mentioned disadvantages of the prior art.

SUMMARY OF THE INVENTION

According to the present invention there is provided a method for determining layer thickness or other parameters of a multilayer structure, comprising the steps of producing an ultrasonic pulse in the multilayer structure for interaction therewith over a range of frequencies to obtain a time-dependent interaction signal characteristic of the multilayer structure; detecting the interaction signal from the said multilayer structure; transforming said time-dependent interaction signal from the time domain to the frequency domain to obtain the frequency response of the said multilayer structure; determining locations of peak or dip values over the range of frequencies from said frequency response of the said multilayer structure to obtain a set of measured resonance frequencies; using a mathematical model describing the behaviour of said multilayer structure and containing at least one variable parameter to predict resonance frequencies for said multilayer structure; and adjusting said at least one variable parameter in said mathematical model to obtain a best fit of said predicted resonance frequencies with said measured resonance frequencies to thereby obtain said at least one variable parameter.

The mathematical model is preferably a characteristic equation derived from appropriate boundary conditions and given by:

$$\begin{vmatrix} B^+T \\ B^- \end{vmatrix} = 0$$

where $|\cdot|$ is the determinant of a matrix, T is the global matrix of the multilayer structure, and matrices $B^+$ and $B^+$ relates to the particular boundary conditions applied on the vectors combining displacements and tractions, of both the top and bottom surfaces.

The invention thus provides an apparatus and method using ultrasonic spectroscopy and a model that can be reduced in a characteristic equation, specifically oriented for predicting resonance frequencies, to determine the thickness, elastic properties and adhesion strength of a general multilayer structure. The method is of particular interest when the thickness of the multilayer structure is less than two millimeters or when the ultrasound is generated by a laser. The use of a characteristic equation is more efficient, and can result in a reduction factor of at least 10 in processing time.

The present invention also provides a system for determining layer thickness and other parameters of a multilayer structure, comprising an ultrasonic pulse generator for generating an ultrasonic pulse in the multilayer structure for interaction therewith over a range of frequencies to obtain a time-dependent interaction signal characteristic of the multilayer structure; a detector for detecting the interaction signal from the said multilayer structure; a spectrum analyzer for transforming said interaction signal into the frequency domain to obtain a measured frequency response; and a processor for calculating from a mathematical model of said multilayer structure predicted resonance frequencies and obtaining a best fit of said predicted resonance frequencies with said measured frequency response by adjusting at least one parameter in said mathematical model, thereby to obtain said at least one parameter.

Preferably, the said spectrum analyzer determines the resonance frequencies and said processor matches the measured resonance frequencies with predicted resonance frequencies from said mathematical model to obtain said at least one parameter.

BRIEF DESCRIPTION OF THE DRAWINGS

The invention will be described in more detail, by way of example only, with reference to the accompanying drawings, in which.

DETAILED DESCRIPTION OF THE PREFERRED EMBODIMENTS OF THE INVENTION

Figure 1A:
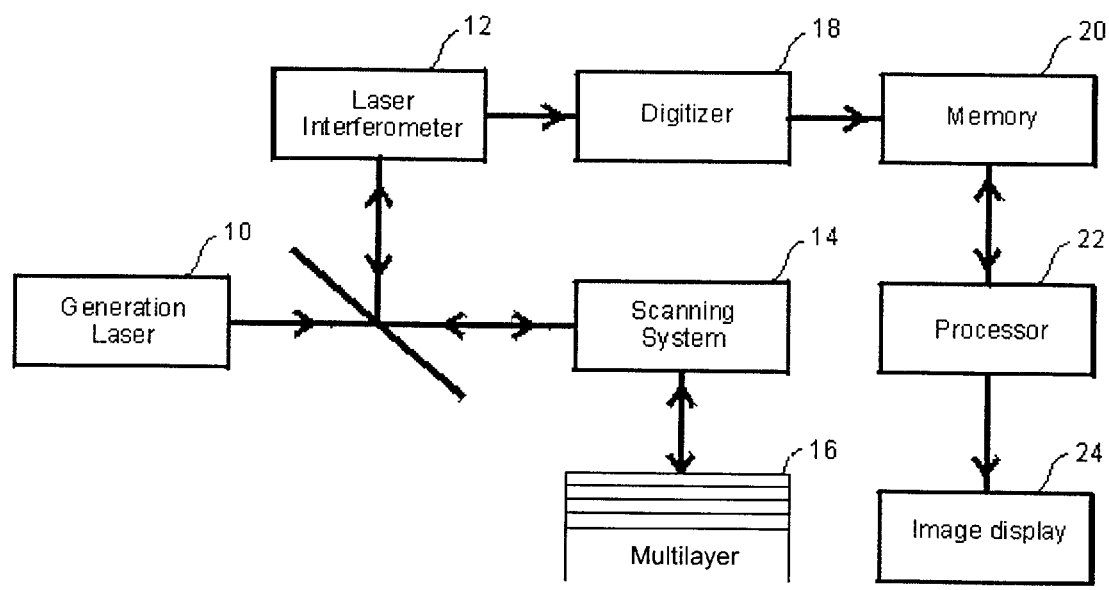
FIG. 1 a) Schematic diagram of a system according to one embodiment of the invention, and b) block diagram illustrating the various steps of the ultrasonic spectroscopy method.

FIG. 1a shows an apparatus according to one preferred embodiment when applying ultrasonic spectroscopy to a multilayer structure. The apparatus is a laser ultrasonic system whereby the generation laser 10 is a pulsed laser source and the laser interferometer 12, used for detecting the ultrasonic signal, comprises a long pulse laser or continuous laser coupled to an optical interferometer, such as a stabilized confocal Fabry-Perot. The two laser beams for generation and detection, are focused at nearly the same location onto the surface. In the preferred embodiment, the ultrasonic pulse is generated in the nondestructive thermoelastic regime, with a large enough laser spot to create resonances of essentially longitudinal waves. Preferably, a scanning system 14 is employed for generating and detecting ultrasound at a plurality of scanning positions constituting the measurement grid at the surface of the multilayer structure 16. In the present embodiment, the array of signals is obtained by scanning the beams on the sample surface with steered mirrors. Alternatively, the sample could be moved using an X-Y translation table. The interaction signal detected at each scanning position on the measurement grid is digitally sampled by a digitizer 18 and stored into a memory 20, thus providing an array of waveform data. Alternatively, an electronic spectrum analyzer can be used to determine and store only resonance frequencies for each scanning position. A processor unit 22 comprising a single or several processors is used to apply the ultrasonic spectroscopy method and obtain thicknesses or other parameters at each scanning position of the multilayer structure. Then, these parameters are displayed in different images provided by a display unit 24.

Figure 1B:
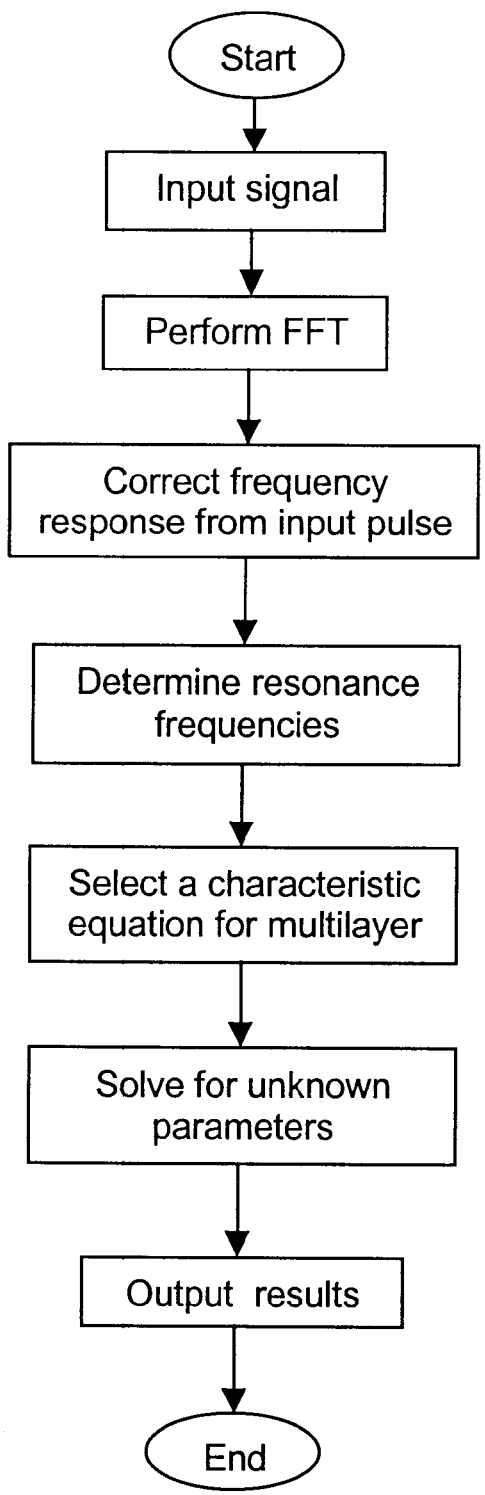
Figure 2:
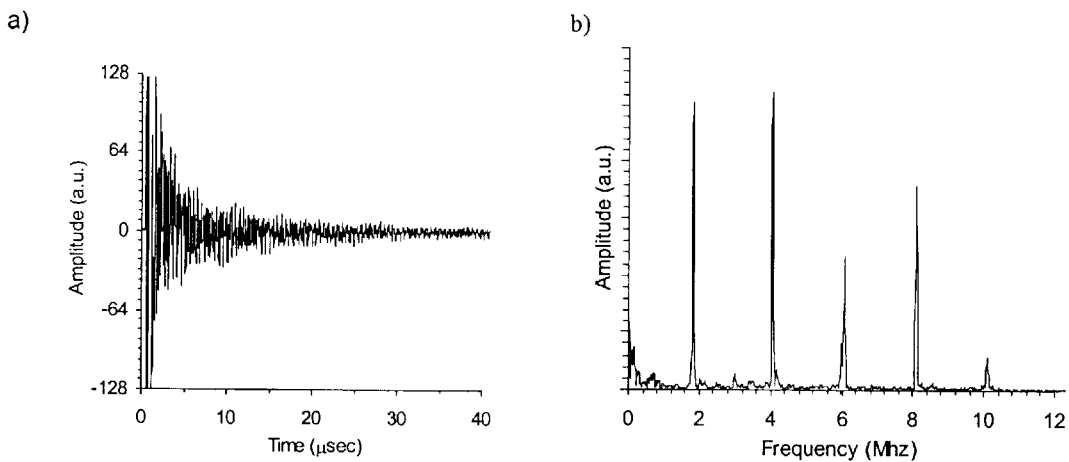
FIG. 2 Typical laser-ultrasonic signal from the two-layer test specimen: a) time signal and b) corresponding frequency spectrum.

FIG. 1b shows an example of implementation of the proposed ultrasonic spectroscopy method applied to a multilayer structure and the various steps it comprises. First, a wideband ultrasonic pulse is launched at one position into the multilayer structure either with a transducer, or with a radiation source like a laser using the system described above. The interaction signal comprising several reflected echoes is collected and transformed into the frequency domain either using Fast Fourier Transform (FFT) after appropriate windowing, or using an electronic spectrum analyzer. The interference between overlapping echoes in the interaction signal produces resonance dips or peaks in the amplitude of the frequency response. In the preferred embodiment, the frequency response is corrected with the frequency spectrum of the input pulse to obtain a frequency response indicative of the multilayer structure alone. A typical recorded signal and its frequency spectrum are shown in FIGS. 2a and 2b. In FIG. 2a, the x-axis represents time (in $\mu s$) and the y-axis represents the amplitude of surface displacement of the multilayer structure on the same side as generation (in arbitrary units). This figure shows the interaction signal comprising typically more than ten echoes. FIG. 2b shows the corresponding frequency response with resonance frequencies characteristic of the multilayer structure clearly observable. Notice that for adhesively bonded layers, the resonance modes of the individual layers are strongly coupled and generally not equally spaced in the frequency domain. Then, a processing method is used to determine the locations of peak values or dip values over the range of frequencies of the input pulse to obtain a set of measured resonance frequencies. Different algorithms have been previously proposed for this purpose and one of them is used. An example consists in fitting a curve (simple function) to the frequency response and determine peak or dip values from the curve. Others could have also been used and have provided similar information.

The set of measured resonance frequencies is then used in conjunction with an adequate model of the multilayer structure to get the unknown parameters. Such a model preferably include a bonding strength parameter between adjacent layers to account for the finite amount of adhesion. Not taking into account this effect may lead to poor estimates of thickness or other parameters. A rigorous and exact approach to modelling the propagation of ultrasound in multilayer structure is used, which is based on the well-known transfer matrix formulation, with recent improvements for speed and numerical stability. The formulation is based on relating displacement and stress (traction) on both sides of each layer composing the multilayer structure with a transfer matrix. Then, rigid boundary conditions applied between adjacent layers lead to the product of layer matrices to form a global matrix which connects the top and bottom surfaces of the multilayer structure. A finite amount of adhesion is introduced in the model by inserting an additional interphase layer between adjacent layers. In the limit of a negligible inertia and thickness compared to the wavelength, this results in a special matrix for the interphase which involves a single bonding strength parameter. As previously, rigid boundary conditions between material or interphase layers are applied to form a global matrix for the multilayer structure. Then, the full ultrasonic response in either the time or frequency domain can be calculated numerically, generally after some algebraic matrix manipulations.

Although this numerical approach can be used for predicting resonance frequencies, the invention provides a more efficient approach based on the use of a characteristic equation whose roots predict the resonance frequencies of the multilayer structure. Such a characteristic equation, more specifically oriented for the analysis of resonances is easier to use and allows a faster processing in determining unknown parameters of the multilayer structure for real-time applications. The bonding parameters involved will be made adjustable in the proposed method when closely matching the set of measured resonance frequencies with predicted resonance frequencies from the model. This characteristic equation is obtained by prescribing boundary conditions on the top and bottom layers in the general matrix form:

$$\begin{bmatrix} B^+q^+ \\ B^-q^- \end{bmatrix} = \begin{vmatrix} B^+T \\ B^- \end{vmatrix} q^- = 0 \qquad (1)$$

where the matrix T is the global matrix of the multilayer structure, and matrices $B^+$ and $B^+$ relates to the particular boundary conditions applied on the vectors combining displacements and tractions, of both the top and bottom surfaces, respectively $q^+$ and $q^-$. Then, for a nontrivial solution to exist, it is required that the determinant of the matrix in eq. (1) vanishes.

As an example of characteristic equation, the case of a two-layer structure, such as paint on metal sheet will be considered. This example takes only into account propagation of longitudinal waves. In the preferred embodiment where the ultrasonic pulse is generated and detected by lasers, one possible application is to determine paint and metal thicknesses, the inspection being performed on the paint surface. The characteristic equation for this system is obtained by applying traction-free boundary conditions on the top and bottom layers:

$$R(f) = \sin(\phi_1 + \phi_2) + r_p\sin(\phi_1 - \phi_2) - t_p\frac{z_2\omega}{S}\sin(\phi_1)\sin(\phi_2) = 0 \qquad (2)$$

where $r_p$ and $t_p$ are the reflection and transmission coefficients given by:

$$r_p = \frac{z_1 - z_2}{z_1 + z_2} \quad t_p = \frac{2z_1}{z_1 + z_2} \qquad (3)$$

and $\phi_i$, $z_i$ and $\omega$ are given by:

$$\phi_i = \frac{\omega d_i}{v_i} \quad z_i = \rho_i v_i \quad \omega = 2\pi f \qquad (4)$$

with $d_i$, $v_i$ and $\rho_i$ respectively the thickness, wave velocity and density of the $i^{th}$ layer, f the ultrasonic frequency and S an adhesion parameter that characterizes bond strength between the two layers. Typically, the parameter S ranges from $10^{12}$ N/m$^3$ for a weak bond to $10^{16}$ N/m$^3$ for a strong bond. The characteristic equation allows us to predict the resonance frequencies present in the ultrasonic signal for given properties and thickness of the different layers.

Figure 3:
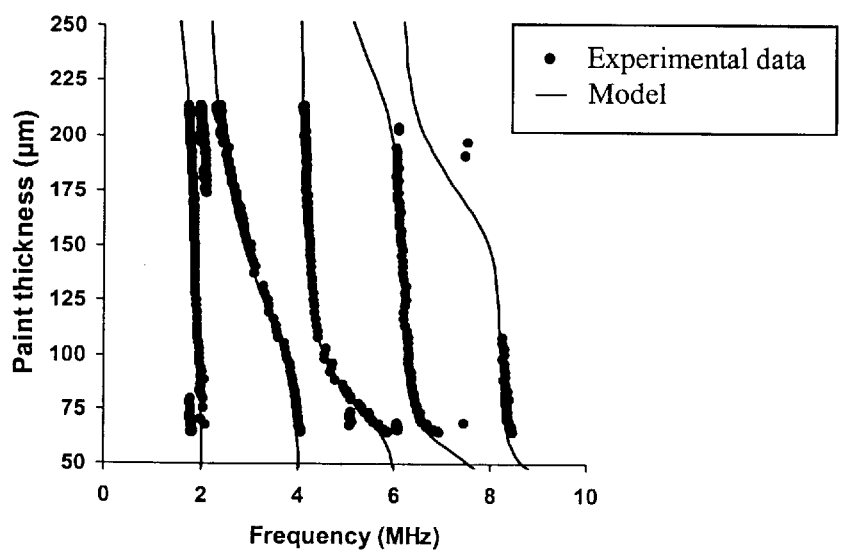
FIG. 3 Resonance frequencies as function of paint thickness on a two-layer test sample.

A test sample was fabricated with a broad variation of paint thickness in order to validate the model. A thick paint layer was applied to a 1.5-mm thick aluminum sheet. By tilting the sample while the paint was drying, a paint thickness varying from 60 $\mu$m to 210 $\mu$m was obtained. The test sample was then inspected with a laser-ultrasonic system with a frequency range between 1 and 12 MHz. FIG. 3 shows the resonance frequencies from the laser-ultrasonic data as function of the paint thickness (data points). Independently, the longitudinal velocity and density of the paint and aluminum sheet were measured. Using these measurement results, the resonance frequencies predicted by the characteristic equation were calculated and are also plotted in FIG. 3. Notice that the only adjustable parameter is the adhesion parameter which sets the bonding strength of the paint on the metal sheet. In this case, a very good fit is obtained with a value $S=10^{14.8}$ N/m$^3$, which corresponds to an intermediate bonding strength, as expected for the peelable paint used. As one can see in FIG. 3, the presence of even a thin paint layer on the surface of the aluminum sheet can have a significant impact on the position of the resonance frequencies. The small difference between the model and the laser-ultrasonic data for paint layer thickness above 175 $\mu$m is caused by the presence of shear wave, not included in the simple model. Also, the difference near 2 MHz for paint thickness lower than 75 $\mu$m may be due to small peaks of noise interpreted as a valid resonance.

From the characteristic equation, a numerical inversion technique can be used to obtain thickness or other parameters of the individual layers from measured resonance frequencies. The problem is to simultaneously and unambiguously determine k unknown parameters $p_1, \ldots, p_k$ from a close matching or best fit of n resonance frequencies using the characteristic equation. Obviously, the number of parameters k to determine must be less than the number of measured resonance frequencies over the range of frequencies of the input pulse. One approach is to perform the fit by minimizing a certain function of merit relating the measured resonance frequencies with those predicted from the characteristic equation. Different functions of merit have been investigated for this purpose. In the preferred embodiment, the function of merit that has provided the best results is:

$$\min_{p_1,\ldots,p_k} \sum_{i=1}^{n} \left| \frac{f_{ex} - f_{th}}{i} \right| \quad (5)$$

where $f_{th}$ are solutions of $R(f_{th})=0$, $f_{ex}$ are the measured values and i is the order of the resonance. Except for the unknown parameters to determine $p_1, \ldots, p_k$, all other parameters are kept constant during the minimization process. Other functions of merit such as least-square fit, or a different weighting function other than 1/i can be used. An alternative approach is to minimize the residues, in the least-square or absolute sense, when inserting the experimental frequencies $f_{ex}$ as solutions of the characteristic equation. This approach using residues is found to be at least 2 times faster but may fail to converge occasionally. Generally for both approaches, the model depends nonlinearly on $p_1, \ldots, p_k$ and therefore, the minimization is multidimensional and must proceed iteratively. Given trial values for the unknown parameters, the procedure improves the solution at each iteration and is repeated until a convergence criterion is met. Different algorithms have been developed for this purpose. Finally, one notices that the method allows for taking into account frequency dependent elastic properties in one or more layers of the multilayer structure. For each measured resonance frequency, appropriate elastic properties can be attributed to each layer when calculating the i th root from the characteristic equation or evaluating the residue. Also using similar arguments, temperature functional dependence of elastic properties and bonding strength between layers composing the multilayer structure can be included.

Figure 4A:
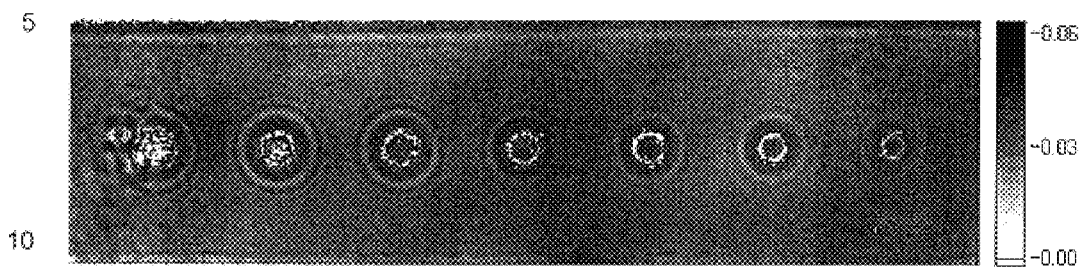
FIG. 4. Thickness maps in mm of a) paint layer and b) aluminum sheet having flat-bottom holes on the opposite side simulating thickness reduction of 19.2%, 14.8%, 9.3%, 5.5%, 2.2%, 1.1% and 0.5% (from left to right).
Figure 4B:
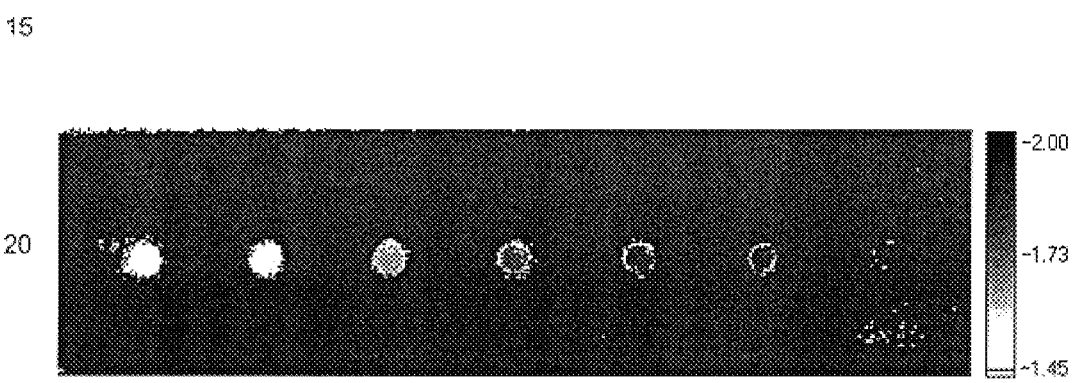
Figure 5:
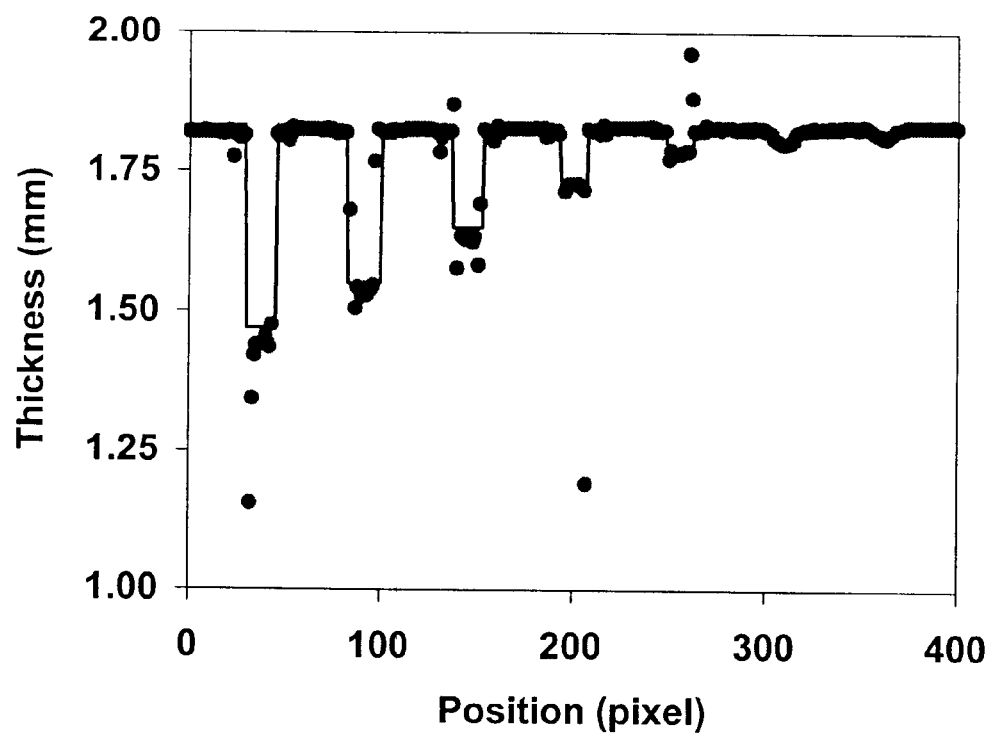
FIG. 5. Cross-section on the aluminum thickness map in FIG. 4b along the line of flat-bottom holes.
Figure 6:
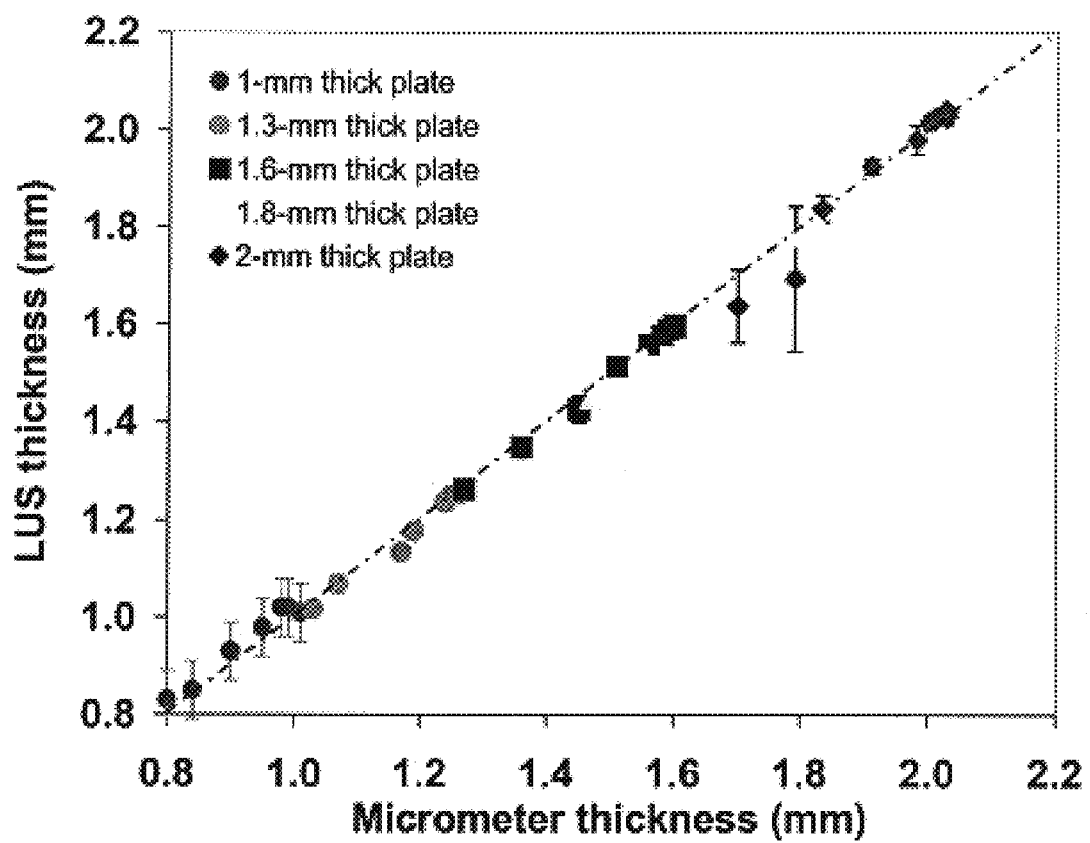
FIG. 6. Comparison between laser-ultrasonic and micrometer measurements of thickness for several test samples with flat-bottom holes.

The method described above was used to determine the thickness of an aluminum sheet with paint applied on it. A sample was built composed of a 2024-T3 aluminum sheet with a nominal thickness of 1.8 mm, having flat-bottom holes to simulate material loss ranging approximately from 0.5% to 20% of the nominal thickness. Prior to inspection with the laser-ultrasonic system, the sample was covered with a thin layer of a latex peelable paint. Then, the above method was applied to each waveform or signal corresponding to different locations on the sample. FIG. 4 shows the laser-ultrasonic thickness maps for both the paint layer and the metal sheet on the various locations. The thickness numbers in FIG. 4 are in mm. The thickness map of the paint layer in FIG. 4a is nearly flat with a value of 35 $\mu$m on areas outside as well as inside the holes. This is with the exception of the hole edges where the laser spot is in a mixed area. The thickness map of the metal layer is shown in FIG. 4b with the grayscale color code for thickness values on the right. The light gray areas correspond to areas with large metal loss, while the dark gray areas corresponds to areas with no metal loss. The "out-of-range" value are coded as white, hence, the hole edges appear clearly on the image as white circles. This figure clearly show the presence of the flat-bottom holes with good estimates of material loss, with the exception of the smallest one. To better evaluate the precision of the method, FIG. 5 shows a cross-section along the line of flat-bottom holes in the metal thickness map in FIG. 4b. The data points corresponds to the pixel values in FIG. 4b and the solid line corresponds to the nominal thickness outside and inside the holes. The agreement is found very good and in addition, the smallest hole on the right is clearly visible here. The sampling length of the full waveform limits the frequency resolution to approximately 0.15 MHz, corresponding to a thickness reduction of approximately 0.3%. The resolution of the laser-ultrasonic data is sufficient to detect a low-level metal loss of less than 1%. Finally, FIG. 6 shows a comparison between laser-ultrasonic and micrometer measurements for several test samples having different nominal thicknesses and flat-bottom holes with different depths. Again, the agreement is very good, with the larger error for the thinnest sample attributable to a lower number of resonances available in the frequency range of the laser-ultrasonic system used.

Of course, numerous other than described above embodiments of the method and system may be envisaged without departing from the spirit and scope of the invention.

What is claimed is:

1. A method for determining layer thickness or other parameters of a multilayer structure, comprising the steps of:

producing an ultrasonic pulse in the multilayer structure for interaction therewith over a range of frequencies to obtain a time-dependent interaction signal characteristic of the multilayer structure;

detecting the interaction signal from said multilayer structure;

transforming said time-dependent interaction signal from the time domain to the frequency domain to obtain the frequency response of said multilayer structure;

determining locations of peak or dip values over the range of frequencies from said frequency response of said multilayer structure to obtain a set of measured resonance frequencies;

using a mathematical model describing the behaviour of said multilayer structure and containing at least one variable parameter to predict resonance frequencies for said multilayer structure, said mathematical model being in the form of a characteristic equation whose roots provide said predicted resonance frequencies; and adjusting said at least one variable parameter in said mathematical model to obtain a best fit of said predicted resonance frequencies with said measured resonance frequencies to thereby obtain said at least one variable parameter.

2. A method according to claim 1, wherein said step of transforming the time dependent signal into the frequency domain is performed by computing the Fast Fourier Transform of said interaction signal.

3. A method according to claim 1, wherein said frequency response includes a correction to take into account the frequency spread of the input pulse to obtain a frequency response which is indicative of the multilayer structure alone.

4. A method according to claim 1, wherein said step of finding the best fit is performed by using a non-linear fitting technique.

5. A method according to claim 1, wherein a bonding strength parameter between adjacent layers is included in said mathematical model.

6. A method according to claim 5, wherein said at least one variable parameter includes layer thicknesses, and said mathematical model includes as known parameters elastic properties and densities of individual layers, as well as said bonding strength parameter.

7. A method according to claim 1, wherein said at least one variable parameter includes several elastic properties of the multilayer structure, and said mathematical model further includes known parameters relating to the properties of the multilayer structure.

8. A method according to claim 5, wherein said at least one variable parameter includes any combination of parameters involved in said mathematical model of the multilayer structure, including the bonding strength parameter between adjacent layers, and said mathematical model further includes known parameters relating to the properties of the multilayer structure.

9. A method according to claim 1, wherein said characteristic equation is given by:

$$\begin{vmatrix} B^+ T \\ B^- \end{vmatrix} = 0$$

where $|\cdot|$ is the determinant of a matrix, T is the global matrix of the multilayer structure, and matrices $B^+$ and $B^+$ relates to the particular boundary conditions applied on the vectors combining displacements and tractions, of both the top and bottom surfaces.

10. A method according to claim 9, wherein said characteristic equation is derived only for longitudinal wave propagation in the multilayer structure and a subset of said measured resonance frequencies is selected accordingly for close matching.

11. A method according to claim 1, wherein the frequency dependent elastic properties in one or more layers of said multilayer structure are accounted for in said mathematical model.

12. A method according to claim 5, wherein the temperature functional dependence of elastic properties and bonding strength between layers composing said multilayer structure are accounted for in said mathematical model.

13. A method according to claim 1, wherein the step of determining said location of peak or dip values includes fitting a curve to said frequency response, and determining said peak or dip values from said curve.

14. A method according to claim 1, wherein the step of determining said location of peak values or dip values is performed by an electronic frequency spectrum analyzer.

15. A method as claimed in claim 1, wherein the ultrasonic pulse is generated by a laser.

16. A method as claimed in claim 1, wherein said best fit is determined by minimizing a function of merit.

17. A method as claimed in claim 6, wherein said function of merit has the form:

$$\min_{p_1,\ldots,p_k} \sum_{i=1}^{n} \left| \frac{f_{ex} - f_{th}}{i} \right|$$

where $f_{th}$ are solutions of $R(f_{th})=0$, $f_{ex}$ are the measured values, i is the order of the resonance and $p_1, \ldots, p_k$ are the unknown parameters to determine, all other parameters being kept constant during the minimization process.

18. A method as claimed in claim 1, wherein said best fit is determined by minimizing residues when measured resonance frequencies are inserted as solutions to the characteristic equation.

19. A method according to claim 1, wherein the multilayer structure is a single plate covered by a paint layer.

20. A method as claimed in claim 1, said multilayer structure is a two-layer structure and said characteristic equation is given by the expression:

$$R(f) = \sin(\phi_1 + \phi_2) + r_p \sin(\phi_1 - \phi_2) - t_p \frac{z_2 \omega}{S} \sin(\phi_1)\sin(\phi_2) = 0$$

where $r_p$ and $t_p$ are the reflection and transmission coefficients given by:

$$r_p = \frac{z_1 - z_2}{z_1 + z_2} \quad t_p = \frac{2z_1}{z_1 + z_2}$$

and $\phi_i$, $z_i$ and $\omega$ are given by:

$$\phi_i = \frac{\omega d_i}{v_i} \quad z_i = \rho_i v_i \quad \omega = 2\pi f$$

where $d_i$, $v_i$ and $\rho_i$ are respectively the thickness, wave velocity and density of the $i^{th}$ layer, f is the ultrasonic frequency and S is an adhesion parameter that characterizes bond strength between the two layers of said structure.

21. A method as claimed in claim 1, wherein said thickness or other parameters are determined for at least one underneath layer of said multilayer structure.

22. A system for determining layer thickness and other parameters of a multilayer structure, comprising:

an ultrasonic pulse generator for generating an ultrasonic pulse in the multilayer structure for interaction therewith over a range of frequencies to obtain a time-dependent interaction signal characteristic of the multilayer structure;

a detector for detecting the interaction signal from said multilayer structure;

a spectrum analyzer for transforming said interaction signal into the frequency domain to obtain a measured frequency response;

a processor for calculating from a mathematical model of said multilayer structure predicted resonance frequencies and obtaining a best fit of said predicted resonance frequencies with said measured frequency response by adjusting at least one parameter in said mathematical model, thereby to obtain said at least one parameter, said mathematical model being in the form characteristic equation whose roots provide said predicted resonance frequencies.

23. A system as claimed in claim 22, wherein said spectrum analyzer determines the resonance frequencies and said processor matches the measured resonance frequencies with predicted resonance frequencies from said mathematical model to obtain said at least one parameter.

24. A system as claimed in claim 22, wherein said spectrum analyzer digitizes said interaction signal first and then performs windowing and smoothing prior to transformation into the frequency domain.

25. A method according to claim 22, wherein said spectrum analyzer includes an electronic part to display the spectrum followed by an analog-to-digital conversion to store either the full frequency response or the measured resonance frequencies.

26. A system as claimed in claim 22, wherein the generator is a pulsed laser.

27. A system as claimed in claim 22, wherein the detector is a long pulse laser or a continuous laser coupled to an optical interferometer.

28. A system as claimed in claim 22, further comprising a scanning arrangement for scanning the ultrasonic pulse over a surface of said structure.

29. A system as claimed in claim 22, wherein said processor calculates a mathematical model of the multilayer structure that consists in a characteristic equation given by:

$$\left| \begin{matrix} B^+ T \\ B^- \end{matrix} \right| = 0$$

where $|\cdot|$ is the determinant of a matrix, T is the global matrix of the multilayer structure, and matrices $B^+$ and $B^+$ relates to the particular boundary conditions applied on the vectors combining displacements and tractions, of both top and bottom surfaces of the structure.

* * * * *